US006245904B1

(12) United States Patent
Melms et al.

(10) Patent No.: US 6,245,904 B1
(45) Date of Patent: Jun. 12, 2001

(54) RECOMBINANT POLYPEPTIDE BASED ON THE PRIMARY SEQUENCE OF THE INVARIANT CHAIN WITH AT LEAST ONE PRIMARY SEQUENCE OF A SPECIFIC T-CELL EPITOPE OR A PROTEIN DERIVATIVE AND NUCLEIC ACIDS CODING FOR THIS RECOMBINANT POLYPEPTIDE

(75) Inventors: Arthur Melms; Georg Malcherek, both of Tübingen (DE)

(73) Assignee: The University of Tubingen, Tubingen (DE)

( * ) Notice: Subject to any disclaimer, the term of this patent is extended or adjusted under 35 U.S.C. 154(b) by 0 days.

(21) Appl. No.: 09/043,293

(22) PCT Filed: Sep. 16, 1996

(86) PCT No.: PCT/DE96/01763

§ 371 Date: Mar. 16, 1998

§ 102(e) Date: Mar. 16, 1998

(87) PCT Pub. No.: WO97/10335

PCT Pub. Date: Mar. 20, 1997

Related U.S. Application Data

(60) Provisional application No. 60/017,663, filed on May 14, 1996.

(30) Foreign Application Priority Data

Sep. 14, 1995 (DE) .............................................. 195 34 170

(51) Int. Cl.$^7$ ............................. C07H 21/04; C12N 1/20; C12N 15/00; C12N 5/06; A01N 43/04

(52) U.S. Cl. .......................... 536/23.4; 435/6; 435/252.3; 435/254.2; 435/320.1; 435/362; 514/44; 514/885

(58) Field of Search ........................ 536/23.4; 435/252.3, 435/320.1, 975, 326, 6, 362, 254.2; 514/885, 44

(56) References Cited

PUBLICATIONS

Sanderson et al. PNAS 92:7217–7221, Aug. 1995.*
Tisch R & McDevitt, M.O. PNAS 91–437–438, Jan. 1994.*
Physicians Desk Reference 53rd Edition Foreword Arky Ronald Medical Economics Company Inc Montvale NJ USA, 1999.*
Merriam–Webster's Collegiate Dictionary 10th Edition p. 870 Merriam–Webster Inc USA, 1993.*

* cited by examiner

*Primary Examiner*—David Saunders
*Assistant Examiner*—Amy DeCloux
(74) *Attorney, Agent, or Firm*—Hardaway/Mann IP Group

(57) ABSTRACT

The present invention is relative to nucleic acids containing at least one nucleic acid sequence coding for a recombinant polypeptide, which recombinant polypeptide contains at least partially the primary sequence of the invariant chain and at least one primary sequence from a specific T-cell epitope and is processed in a desired manner in antigen-presenting cells for binding the specific T-cell epitope to MHC II molecules.

12 Claims, 1 Drawing Sheet

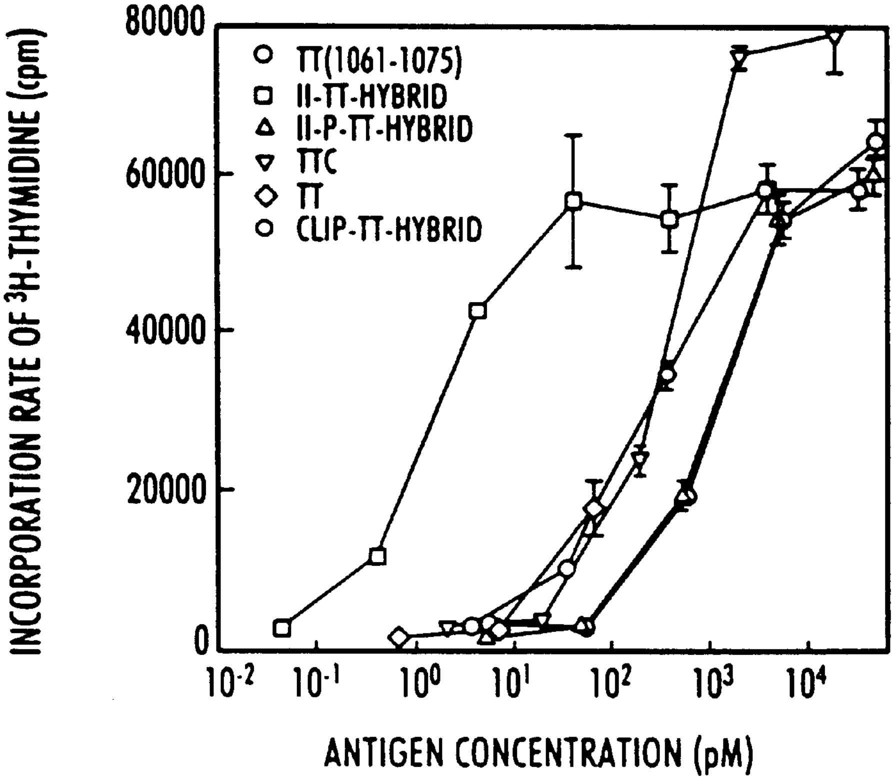
Fig. 1
Fig. 2
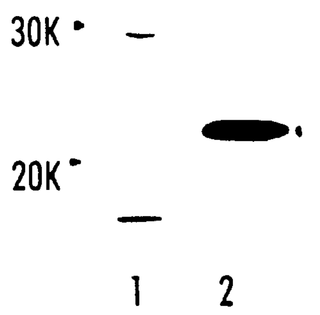

SEQUENCE LISTING

```
<160> NUMBER OF SEQ ID NOS: 3

<210> SEQ ID NO 1
<211> LENGTH: 30
<212> TYPE: PRT
<213> ORGANISM: Homo sapiens

<400> SEQUENCE: 1

Leu Pro Lys Pro Pro Lys Pro Val Ser Lys Met Arg Met Ala Thr Pro
  1               5                  10                  15

Leu Leu Met Gln Ala Leu Pro Met Gly Ala Leu Pro Gln Gly
             20                  25                  30


<210> SEQ ID NO 2
<211> LENGTH: 9
<212> TYPE: PRT
<213> ORGANISM: Clostridium tetani

<400> SEQUENCE: 2

Ile Arg Glu Asp Asn Asn Ile Thr Leu
  1               5


<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: "Ii-P-TT
      hybrid" peptide: aa 6 to 16: core peptide of T-cell epitope of
      tetanus toxin; aa 1 to 5, and 15 and 16: from CLIP region of
      invariant chain isoform p35

<400> SEQUENCE: 3

Lys Pro Val Ser Lys Ile Arg Glu Asp Asn Asn Ile Thr Leu Gln Ala
  1               5                  10                  15
```

RECOMBINANT POLYPEPTIDE BASED ON THE PRIMARY SEQUENCE OF THE INVARIANT CHAIN WITH AT LEAST ONE PRIMARY SEQUENCE OF A SPECIFIC T-CELL EPITOPE OR A PROTEIN DERIVATIVE AND NUCLEIC ACIDS CODING FOR THIS RECOMBINANT POLYPEPTIDE

This application is a national stage filing under 35 USC 371 from PCT/DE96/01763, filed Sep. 16, 1996. This application claims the benefit of U.S. Provisional Application No. 60/017,663, filed May 14, 1996.

FIELD OF THE INVENTION

The present invention is relative to nucleic acids containing at least one nucleic acid sequence coding for a recombinant polypeptide, which recombinant polypeptide contains at least partially the primary sequence of the invariant chain and at least one primary sequence from a specific T-cell epitope or from a protein and is processed in a desired manner in antigen-presenting cells for a binding of the specific T-cell epitope to MHC class II molecules.

No suitable vaccines are available against numerous pathogens. In the traditional methods of vaccination dead or attenuated pathogens are used as vaccine. In order to prevent undesired side effects or even the outbreak of an illness the attempt was made in individual instances to limit vaccines to a few defined antigens which can be produced by molecular, biologic methods in almost pure form and to nevertheless assure an efficient vaccine protection (e.g. hepatitis B vaccination with a recombinant HBsAg ("hepatitis B surface antigen")).

BACKGROUND OF THE INVENTION

The vaccines previously known in the state of the art tend to bring forth side effects, among other things on account of the broadness of their immunogenicity. For example, a single viral or bacterial antigen usually consists of several hundred amino acids whereas T-cells recognize only a small section (<20 amino acids).

In order to utilize the specificity of T-cells, vaccines with a peptide base were developed, among other things. However, peptides have several disadvantages such as a short half-life, an unpredictable and non-specific distribution in the organism, low uptake into the cell and an unclear processing pathway. These factors obligatorily mean that from a physiological standpoint very high concentrations of peptides must be used in order to achieve a desired immune response. This naturally sharply limits the use of peptides as specific immunotherapeutic agents.

Antigens are presented as protein fragments on the surface of so-called "antigen-presenting cells" and are recognized by T-lymphocytes as effector cells. The MHC class I and class II molecules function thereby as peptide receptors in the antigen-presenting cells. In order to assure a functional dichotomy the MHC molecules are loaded in an exactly regulated manner in certain MHC loading compartments with the processed antigen peptides.

MHC molecules are representatives of a polymorphous gene family which is chromosomally coded in a special region, the major histocompatibility complex, "MHC". The MHC molecules in humans are designated as HLA (human leucocyte antigen) molecules. MHC class I molecules are loaded directly at the site of biosynthesis with de novo translated virus or tumor antigens but also with endogenous, cytosolic protein fragments. In contrast thereto, MHC class II molecules (designated in the following in brief as "MHC II molecules") are charged in cellular compartments which communicate with the extracellular environment. In humans the MHC II molecules comprise the HLA-DR, HLA-DQ and HLA-DP molecules, which occur in various genetically coded alleles. Thus, e.g. bacterial antigens from the extracellular environment can be taken up and be presented after intracellular processing in the antigen-presenting cells on their cell surface.

In order to assure an effective immunosurveillance the physiology of the MHC molecules is designed in such a manner that they can present as broad a spectrum of antigenic peptides as possible. Consequently, the copy number of a defined antigenic peptide on the cell surface of antigen-presenting cells is very low (magnitude $10^2$ of a defined antigenic peptide given a total population of approximately $10^5$ peptide receptors). This means that a very heterogenous mixture consisting of a plurality of various antigenic peptides bound to MHC molecules ("peptide ligands") is exposed on the cell surface of the antigen-presenting cells.

Experimental attempts to produce defined MHC/peptide complexes were based up to the present on the expression of recombinant MHC molecules e.g. in the Baculovirus- or *E. coli* expression system. These MHC II molecules have an empty binding groove and can be charged in vitro with suitable peptides. The binding/loading efficiency can vary greatly and can be used only for in vitro tests.

Another attempt starts with recombinant MHC II molecules which, constructed as fusion protein (of the β chain), terminally exhibit a desired ligand via a flexible linker. This ligand segment spontaneously fills the binding groove, so that a more or less large number of MHC II molecules carries this defined peptide ligand as a function of the cell type used. This attempt is limited to the DNA transfection of host cells whereas a direct application on the protein level is not possible.

SUMMARY OF THE INVENTION

Thus, the present invention has the problem of reinforcing the antigenicity of proteins and/or of reducing the (intrinsic) heterogeneity of MHC II antigenic peptide complexes of antigen-presenting cells while avoiding, among other things, the above-mentioned disadvantages of the vaccination methods described in the state of the art. In particular, a novel system for a directed and highly specific stimulation of the immune system by means of exactly definable antigenic peptides should be made available in order e.g. to improve the vaccinations of mammals.

This problem is solved by the embodiments of the present invention characterized in the claims. In particular, a nucleic acid is made available in a first embodiment in accordance with the invention which contains at least one nucleic acid sequence coding for a recombinant polypeptide, which recombinant polypeptide contains at least partially the primary sequence of the invariant chain and at least one primary sequence from a specific T-cell epitope which is inserted into the area of the invariant chain comprising the CLIP sequence and which recombinant polypeptide is processed in such a manner in antigen-presenting cells that the specific T-cell epitope is produced and binds to MHC II molecules.

In a further embodiment of the invention a nucleic acid is made available which contains at least one nucleic acid sequence coding for a recombinant polypeptide, which recombinant polypeptide contains at least partially the primary sequence of the invariant chain and at least one primary sequence from a specific T-cell epitope, with at least one amino acid of the area of the invariant chain comprising the CLIP sequence being deleted and replaced by the T-cell epitope, and which recombinant polypeptide is processed in such a manner in antigen-presenting cells that the specific T-cell epitope is produced and bonds to MHC II molecules.

BRIEF DESCRIPTION OF THE DRAWINGS

FIG. 1 of the drawings is a graph setting forth data related to the processing of a recombinant Ii-TT hybrid protein.

FIG. 2 of the drawings is an SDS-PAGE of NI-NTA-purified Ii-TT hybrid protein.

DETAILED DESCRIPTION

The concepts "nucleic acid" and "nucleic acid sequence" signify natural or semisynthetic or synthetic or modified nucleic acid molecules of deoxyribonucleotides and/or ribonucleotides and/or modified nucleotides.

The concept "recombinant polypeptide" or "hybrid protein" signifies a construct produced with molecular biological techniques based on the natural DNA of the original genome or the natural DNA modified with a heterogeneous DNA sequence and with which it can be combined, e.g. with plasmids, and can be replicated and expressed in a suitable host system.

The concept "T-cell epitope" signifies an antigenic/immunogenic sequence of a protein which brings about an activation of T-lymphocytes and comprises in accordance with the invention the primary sequence of the T-cell epitope or the primary sequence of an (antigenic) polypeptide or protein or antigen which contains at least one primary sequence of a T-cell epitope. T-lymphocytes recognize this stimulus with the aid of a T-cell receptor normally in the form of a peptide bound to MHC molecules. T-cell epitopes can also bring about only a partial activation in certain instances, in which a decoupling of various processes associated with the T-cell activation can take place. This can concern the decoupling of the proliferative or cytotoxic vis-à-vis the spilling out of individual mediator substances (lymphokines) or [can concern] their qualitative or quantitative composition. This type of ligands exhibit, in comparison to conventional T-cell epitopes, slight changes in their primary sequence (e.g. substitution of individual amino acids) and are designated in the literature as "altered peptide ligands", "APLs". Under experimental conditions an immunotherapeutic potential is ascribed to APLs.

One embodiment of the present invention concerns in particular the modulation of a subpopulation of T-lymphocytes which is characterized by the expression of the feature CD4 and recognizes the antigens through so-called MHC II molecules. These T-cells are designated in the terminology as "MHC class II restricted". CD4 lymphocytes comprise the most important regulatory T-cell population which are included in a plurality of so-called T-cell-dependent immunoreactions. This includes, in addition to physiological tasks such as the combatting of and elimination of pathogens and degenerated (malignant or endogenous) cells by immunoreactions and interactions to form high-affinity antibodies by B-lymphocytes producing immunoglobulins, the participation in pathological immunoreactions such as tissue-graft-rejection and organ-specific auto-immune diseases such as rheumatoid arthritis (RA), juvenile insulin-dependent diabetes mellitus (IDDM), multiple sclerosis (MS) and a plurality of other diseases of humans in which an immunopathogenesis has been demonstrated.

The functional feature "processing of the recombinant polypeptide in antigen-presenting cells" signifies the intracellular degradation of antigenic proteins in units which can be presented finally associated with MHC molecules on the cell surface. The processing of MHC class II restricted antigens takes place in distinct cellular compartments which are designated as endosomal-lysosomal compartments or "class II compartment" or "class II loading compartment". MHC II molecules, invariant chain and/or their degradation products, HLA-DM and antigenic peptides are concentrated there as minimal functional elements. In general, a function in the antigen processing is conceded to proteinases such as cathepsin D and E which have their optimum activity at an acidic pH.

In the embodiments of the invention the recombinant polypeptide contains at least partially the primary sequence of the invariant chain. The concept invariant chain (Ii) designates a preserved polypeptide associated e.g. with all previously investigated MHC class II alleles and isotypes from humans and mice. The invariant chain exists in four isoforms, p33, p35, p41 and p 43, whose sequence is coded outside of the MHC locus. It exercises its regulatory function in the antigen processing pathway by their association in the endoplasmatic reticulum with MHC II molecules immediately after their biosynthesis. It supports as chaperoning (companion molecule) the association of the MHC $\alpha$ and $\beta$ subunits and in a complex with MHC II molecules it prevents the premature loading of the binding groove of the MHC II molecules with protein fragments. Signal sequences of the invariant chain lead this complex into the "class II loading compartment". After a step-by-step degradation of the invariant chain the MHC II molecules can be loaded, at which time peptides from the invariant chain associated with MHC II molecules ("CLIPs", "class II associated invariant chain peptides") appear as intermediate.

The invariant chain is one of the first proteins which associate in the endoplasmastic reticulum with MHC II molecules, and, what is especially important in this context, remains associated with the MHC II molecules until a so-called "class II loading compartment" is reached. It is assumed that the invariant chain is degraded by proteolytic activity in this distinct cellular subcompartment in which a number of regulation factors such as e.g. the invariant chain and its breakdown products, HLA-DM, MHC II molecules and antigens concentrate, at which time a complex of MHC II molecules with peptide derivatives of the invariant chain (so-called "CLIPs") occurs. The bonding of the CLIPs to the MHC II molecules has already been extensively investigated and it was determined in our own research that the CLIP sequence contains so-called "supermotives" which make it possible for the CLIPs to bind independently of the allele type or isotype in the MHC II peptide binding groove in a manner similar to conventional ligands.

In the embodiments of the invention the recombinant polypeptide coded by the previously defined nucleic acid sequence contains at least partially primary sequences of the natural invariant chain, with a T-cell epitope defined above being inserted into the area of the natural invariant chain comprising the CLIP sequence. Furthermore, the area of the variant chain comprising the CLIP sequence can be at least partially deleted and replaced by a desired T-cell epitope.

The expression "area comprising the CLIP sequence" signifies a section in the natural invariant chain which comprises the CLIP region from the amino acid positions 97 to 126 (relative to the isoform p35 starting with the first start codon) with the sequence

L P K P P K P V S K M R M A T P L L M Q A L P M G A L P Q G and optionally N- and/or C-terminal areas flanking the CLIP region which areas do not adversely influence the antigen processing upon insertion from a desired T-cell epitope or upon deletion and substitution by a desired T-cell epitope. Suitable T-cell epitopes are preferably inserted into the CLIP region of amino acid positions 97–126, more preferably 107–115, of the natural invariant chain and at least one amino acid of this area deleted and replaced by the T-cell epitope. Of course, on the nucleic acid level the constructs produced by traditional genetic engineering methods and containing the nucleic acid of the invention must have the proper reading frame for the desired expression of the recombinant polypeptides.

Further subject matter of the present invention is constituted by a vector containing the nucleic acid of the invention and defined above for the expression of the recombinant polypeptide in prokaryotic or eukaryotic host cells. The vector of the invention can preferably contain suitable regulatory elements such as promoters, enhancers, termination sequences. The vector of the invention can be e.g. an expression vector or a vector for the preferably stable integration of the nucleic acid of the invention into the genetic material of a host cell. A suitable expression system is, e.g. the Baculovirus system, the *E. coli* expression system and expression vectors for mammal cells such as e.g. vectors based on vaccinia-, adeno-, SV40- or on retroviruses.

Further subject matter of the present invention is constituted by a host cell containing the nucleic acid of the invention or the vector of the invention. Suitable host cells are e.g. prokaryontes such as *E. coli,* or eukaryotic host cells such as COS-, Hela-, CHO cells, especially antigen-presenting cells of mammals. For a sufficient expression rate the nucleic acid of the invention is either stably integrated in the genetic material of the host cell or the vector of the invention contains suitable regulatory sequences for replication, transcription and/or translation in vivo and/or in vitro, that is, in the cell-free system too.

Further subject matter of the invention is constituted by the recombinant polypeptide itself which is coded by the previously defined nucleic acid sequence, which sequence can be degenerated in accordance with the genetic code. The recombinant polypeptide of the invention can be modified in vitro by post-translational reactions in vivo or by chemical and/or enzymatic methods known in the state of the art.

The nucleic acid sequence or hybrid DNA of the invention, the vector of the invention and the recombinant polypeptide of the invention can be produced by methods known in the state of the art. For example, the hybrid DNA can be cloned into a suitable expression vector (e.g. pQE31, Diagen company, Hilden, Germany) and competent M15 cells as host cells can be transformed by means of the $CaCl_2$ method. Transformed cells are selected by means of their resistance to ampicillin and used as individual colonies for cultivation in a liquid medium. After induction with IPTG the recombinant protein is produced and purified after 3 hours from the cell lysate by means of metal affinity chromatography.

Further subject matter of the present invention is constituted by a pharmaceutical composition containing the nucleic acid of the invention or the recombinant polypeptide and optionally at least one pharmaceutically compatible carrier.

The nucleic acid of the invention can function as a universally applicable vehicle for reinforcing and homogenizing the antigen presentation for, in particular, CD4 positive T-cells of mammals, preferably of humans. T-cell epitopes of any origin can be guided into the loading compartment for the MHC II molecules by the recombinant polypeptide of the invention, at which time the T-cell epitopes from the recombinant polypeptide are processed proteolytically via processing signals and presented via intrinsic bonding properties on MHC II molecules.

The homogenization of the T-cell epitopes on the surface of antigen-presenting ("immunocompetent") cells can be used for investigating the autoreactive potential on the T-cell level. In such a diagnostic use the T-cell epitopes are used as probes for a possible predisposition for autoimmune diseases. Known T-cell epitopes can be used as probe for a predisposition to, e.g., rheumatic arthritis, multiple sclerosis, insulin-dependent diabetes mellitus, myasthenia gravis. Thus, further subject matter of the present invention is constituted by a diagnostic kit for demonstrating autoimmune diseases which contains at least the nucleic acid of the invention or the recombinant polypeptide of the invention.

Furthermore, either the recombinant polypeptide expressed by the nucleic acid of the invention in antigen-presenting cells or the recombinant polypeptide of the invention itself can be used for a highly specific and selective vaccination by being taken up into the antigen-presenting cell and subsequent specific processing and presentation of the desired T-cell epitope(s). Such a vaccination, initiated by the nucleic acid of the invention or the recombinant polypeptide of the invention surprisingly has the following advantages:

Only a certain T-cell epitope or antigenic fragment is selectively and highly specifically produced by the intracellular processing of the recombinant polypeptide. The processing efficiency of a T-cell epitope contained in the recombinant polypeptide of the invention is on the order of several magnitudes greater; that is, an application with a tailored-to-measure antigen or antigenic peptide shows in vivo a clearly greater vaccination efficiency with clearly reduced molar vaccine doses.

The vaccination with a hybrid consisting of parts of the invariant chain and a known antigen containing T-cell epitopes is possible without T-cell epitopes having to be exactly defined. This attempt should be useful in the combatting of intracellular pathogens (viruses, parasites, mycobacteria) and in reinforcing the T-cell response to tumor antigens.

The possibility of the application of defined T-cell epitopes permits a focused and specific intervention in allergic reactions with the goal of desensitizing allergen-specific T-cells. In an analogous manner this attempt should also be possible in the case of autoimmune diseases as well as in the controlling of transplant rejections.

Furthermore, the recombinant polypeptide of the invention can be used for modulating the immune response by means of self, foreign and designer peptides; such a modulation can be carried out more efficiently on account of the previously cited advantages of the recombinant polypeptide of the invention. Moreover, the activation state of T-cells can be influenced by the integration of so-called "altered peptide ligands (APL)" as T-cell epitopes in the recombinant polypeptide of the invention.

FIG. 1 shows the titration curves of various forms of administration of the tetanus toxin (TT) and of the antigenic peptides/polypeptides of *Clostridium tetani;* the incorporation rate of $^3$H-thymidine as a measure of the T-cell proliferation is shown as a function of the antigen concentration. The basal proliferation without the addition of an antigen is approximately 1,500 cpm. The antigenic TT peptide TT(1061–1075) contains the T-cell epitope. The Ii-TT hybrid contains the core sequence TT (1064–1072) instead of the CLIP core sequence Ii (107–115) of the invariant chain. TTC is a recombinant polypeptide of the C fragment of TT, which naturally contains the antigenic TT peptide TT(1061–1075). The CLIP-TT hybrid is a hybrid of a CLIP peptide in which the CLIP core sequence was exchanged for the core epitope TT (1061–1075). In the case of the Ii-P-TT hybrid the portion of the CLIP sequence on the N-terminus is shortened.

FIG. 2 is a Coomassie Blue staining of an SDA polyacrylamide gel with representation of a recombinant Ii-TT hybrid protein after purification via a metallo affinity chromatography.

Track 2 shows the recombinant Ii-Tt hybrid protein as a single band at a molecular weight of about 22 kilodaltons (kD). Molecular weight markers with 20 kD and 30 kD are shown in track 1.

The present invention is explained in more detail in the following example.

EXAMPLE

A well-characterized T-cell epitope from tetanus toxin is integrated into the sequence of the invariant chain. This hybrid antigen enhances the MHC class II restricted T-helper cell response in comparison to the natural antigen and to the recombinant C fragment by several orders of magnitude.

The system in which the highly efficient processing of the hybrid protein is demonstrated uses as antigen the toxin from *Clostridium tetani,* from which a T-cell epitope is integrated into the invariant chain as processing unit. The primary sequence of this tetanus toxin is known (Eisel et al., EMBO J., 1986), likewise a plurality of antigenic determinants generated therefrom for human T-cells.

The T-cell epitope TT (1061–1075) of this tetanus toxin was recently demonstrated as dominant T-cell epitope for T-cells from DR17-positive donors (Malcherek et al., in print). The restriction element for the recognition of TT(1061–1075) is the MHC class II molecule HLA-DR17. The specific contact sites to the HLA-DR17 molecule on the one hand [side] (so-called anchors) and to the T-cell receptor on the other hand (T-cell receptor contact sites) can be dissociated with the aid of alanine-substituted peptide analogues and fixed onto a core epitope of nine amino acids (I R E D N N I T L) within the fifteen amino acid sequence of the Ii-P-TT hybrid (Malcherek et al., in print). The additional amino acids outside of this core sequence of the TT peptide stabilize the bond to the MHC molecule as a rule without these amino acid side chains interacting in a specific manner with the MHC molecule (Malcherek et al., J. Immunol. 1994, 153: 1141).

The titration curves of various forms of administration of the tetanus toxin or of the antigenic peptide/polypeptides show the antigenic nature of the Ii-TT hybrid protein, which, in addition, has a dramatically reinforced immunogenicity in comparison to the native antigen and to the recombinant C fragment of the TT (see FIG. 1). This reinforcing effect is all the more remarkable in view of the fact that the dominant T-cell epitope TT(1061–1075) of the tetanus toxin is already very efficiently processed in its physiological environment in the native toxin and recognized by specific T-cells (Malcherek et al., in print). This state of affairs is illuminated by the low antigen concentrations in the picomolar range which are necessary to stimulate T-cells in vitro to a half-maximal proliferation capacity (see FIG. 1). The specificity of the stimulation of the T-cell clone can be demonstrated by another recombinant Ii construct which does not stimulate the T-cells to proliferation.

Moreover, it can be shown by means of two further hybrid peptides that the core sequence is in fact sufficient for an optimal stimulation (see FIG. 1). These hybrid peptides are conceived in such a manner that the core sequence from the tetanus toxin is flanked by amino acids from the CLIP peptides. This should imitate the situation which is expected in the processing of the hybrid antigen. The shorter peptide KPVSK-TT(1064–1072)-QA ("Ii-P-TT hybrid") stimulates in a manner similar to and just as well as the original T-cell epitope TT(1061–1075). On the other hand, the longer peptide, which represents as it were a CLIP hybrid ("CLIP-TT hybrid"), clearly has a stronger antigenic potential than TT(1061–1075).

This data is a reliable indication that sequences of the CLIP region outside of the core sequence of Ii(107–115) can reinforce the antigenicity of the core sequence of the T-cell epitope. A further reinforcing action of the antigenicity of the hybrid protein in comparison to the native protein and to the recombinant C fragment is supplied by the sequences for an optimal processing of the T-cell epitopes which sequences are located on the invariant chain.

This data also shows that antigenic sequences instead of CLIP sequences are effectively processed in Ii hybrid constructs and dramatically reinforce the MHC class II restricted T-cell response on a molar basis.

1. Construction of the Plasmid DNA Cassette pQE31/Ii-TT

The cDNA of p35 Ii (pcDV$_1$, Strubin et al., 1986) is amplified with 5'- and 3'-specific oligonucleotide primers in such a manner that only the coding sequence can be subcloned by means of newly introduced EcoRI restriction cleavage sites in pBluescript KS$^{+}$" (company Stratagene, Heidelberg, Germany). An NspV restriction cleavage site is generated by means of oligonucleotide-directed, site-specific mutagenesis, based on polymerase chain reaction (PCR), and the further 3'-removed/located NcoI restriction cleavage site destroyed. This Ii mutant, which codes the original protein sequence of Ii, is deleted by NspV/NcoI cleavage around the CLIP core sequence of Ii (107–115) (the nomenclature is relative to the translation start in the case of methionine 1 of the native Ii). The oligonucleotides coding for the core sequence of the T-cell epitope (TT(1064–1072)) from the tetanus toxin are ligated into this Ii cassette. The PstI/BamHI fragment is subsequently subcloned in pQE31 (company Diagen, Hilden, Germany), a bacterial expression vector, yielding the plasmid DNA cassette pQE31/Ii-TT.

2. Expression of the Recombinant Polypeptide Ii-TT

The expression of the recombinant Ii-TT hybrid protein takes place essentially in accordance with the instructions for the QIA express system (company Diagen, Hilden, Germany). Competent *E. coli* M15 cells are transformed with pQE31/Ii-TT and 100 ml bacterial culture induced at $OD_{600}$ from 0.5 with IPTG. After 3 h the cell pellet is lysed in 20 ml 6M guanidinium hydrochloride and the supernatant purified after ultracentrifugation (21,500 rpm, TI45) chromatographically over an Ni-NTA metallo affinity column (company Diagen, Hilden, Germany). The pH 4.5 eluate is analyzed by SDS polyacrylamide gel electrophoresis (SDS-PAGE). The Coomassie Blue staining shows an individual band at 22 KD without visible bacterial contaminants. (The identity of the Ii-TT protein hybrid was corroborated by ELISA with the Ii-specific monoclonal antibodies M-B741 (gift from Dr. Rieber, Institute for Immunology, Munich) and SD$_3$253.74 (gift from Dr. H. Kalbacher, Physiological-Chemical Institute, University of Tubingen).)

What is claimed is:

1. A nucleic acid containing at least one nucleic acid sequence coding for a recombinant polypeptide which recombinant polypeptide contains at least partially the primary sequence of the invariant chain and at least one primary sequence from a specific T-cell epitope which is inserted into the area of the invariant chain comprising the CLIP sequence and which recombinant polypeptide is processed in such a manner in antigen-presenting cells that the specific T-cell epitope is produced and bonds to MHC II molecules.

2. A nucleic acid containing at least one nucleic acid sequence coding for a recombinant polypeptide, said recombinant polypeptide containing at least partially the primary sequence of the invariant chain and at least one primary sequence from a specific T-cell epitope, said at least one primary sequence from a specific T-cell epitope being inserted into the area of the invariant chain comprising the CLIP sequence, with at least one amino acid of the area of the invariant chain comprising the CLIP sequence being deleted and replaced by the T-cell epitope, and which recombinant polypeptide is processed in such a manner in antigen-presenting cells that the specific T-cell epitope is produced and bonds to MHC II molecules.

3. The nucleic acid according to claim 1 with the area comprising the CLIP sequence being the amino acid positions 97 to 126 of the invariant chain.

4. The nucleic acid according to claim 1 with the T-cell epitope from a self-protein or from a viral, prokaryotic or eukaryotic antigen.

5. A vector containing the nucleic acid of claim 4 for expressing the recombinant polypeptide in prokaryotic or eukaryotic host cells.

6. The nucleic acid according to claim 1 wherein said nucleic acid is contained within a host cell.

7. The host cell according to claim 6 in which the recombinant polypeptide is expressed.

8. A diagnostic kit for autoimmune diseases containing the nucleic acid of claim 1.

9. The nucleic acid according to claim 2 with the area comprising the CLIP sequence being the amino acid positions 97 to 126 of the invariant chain.

10. The nucleic acid according to claim 2 with the T-cell epitope from a self-protein or from a viral, prokaryotic or eukaryotic antigen.

11. The nucleic acid according to claim 3 with the T-cell epitope from a self-protein or from a viral, prokaryotic or eukaryotic antigen.

12. A pharmaceutical composition comprising:

the nucleic acid according to claim 1; and a pharmaceutically compatible carrier.

* * * * *